US00PP33239P2

(12) United States Plant Patent
Van Swieten

(10) Patent No.: US PP33,239 P2
(45) Date of Patent: Jul. 6, 2021

(54) ***PHALAENOPSIS* ORCHID PLANT NAMED 'PHALOHCAE'**

(50) Latin Name: ***Phalaenopsis* hybrid**
Varietal Denomination: PHALOHCAE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,005

(22) Filed: Feb. 3, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALOHCAE', particularly characterized by small, yellow-green flowers with greenish-yellow lips, slightly raised calluses, more than two peduncles, and is propagated by meristem tissue culture, is disclosed.

3 Drawing Sheets

Genus and species: *Phalaenopsis* hybrid.
Variety denomination: 'PHALOHCAE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALOHCAE'.

The new *Phalaenopsis* plant is a product of a planned breeding program conducted by the inventor in Bleiswijk, the Netherlands. The objective of this breeding program was to create a new, short *Phalaenopsis* plant with numerous attractive and unique small, greenish-yellow flowers with greenish-yellow lips, suitable for potted plant production.

The new *Phalaenopsis* plant 'PHALOHCAE' is a result of cross-pollination made by the inventor in November 2010 in Bleiswijk, the Netherlands, of the proprietary female, or seed parent, *Phalaenopsis* hybrid '21864-012' (unpatented) with the proprietary male, or pollen parent, *Phalaenopsis* hybrid '32980-05' (unpatented).

The new *Phalaenopsis* was selected by the inventor as a single plant within the progeny of the stated cross-pollination in a controlled greenhouse in Bleiswijk, the Netherlands, in November 2013. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 30, 2019 (Application no. 2019/2069), by Applicant who obtained the subject matter disclosed directly from the inventor. 'PHALOHCAE' has not been made publicly available or sold anywhere in the world prior to the effective filing date of this application with the exception of sales or disclosures made one year or less before the effective filing date of this claimed invention by Applicant who obtained 'PHALOHCAE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALOHCAE' as a new and distinct variety of *Phalaenopsis* plant:

1) Small, yellow-green flowers with greenish-yellow lips;
2) Slightly raised calluses; and
3) Plant has more than two peduncles.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in December 2020. Colors in the photographs may differ from the color values cited in the detailed botanical description, which accurately describe the actual colors of the new variety.

DESCRIPTION OF THE NEW VARIETY

Figure 1:
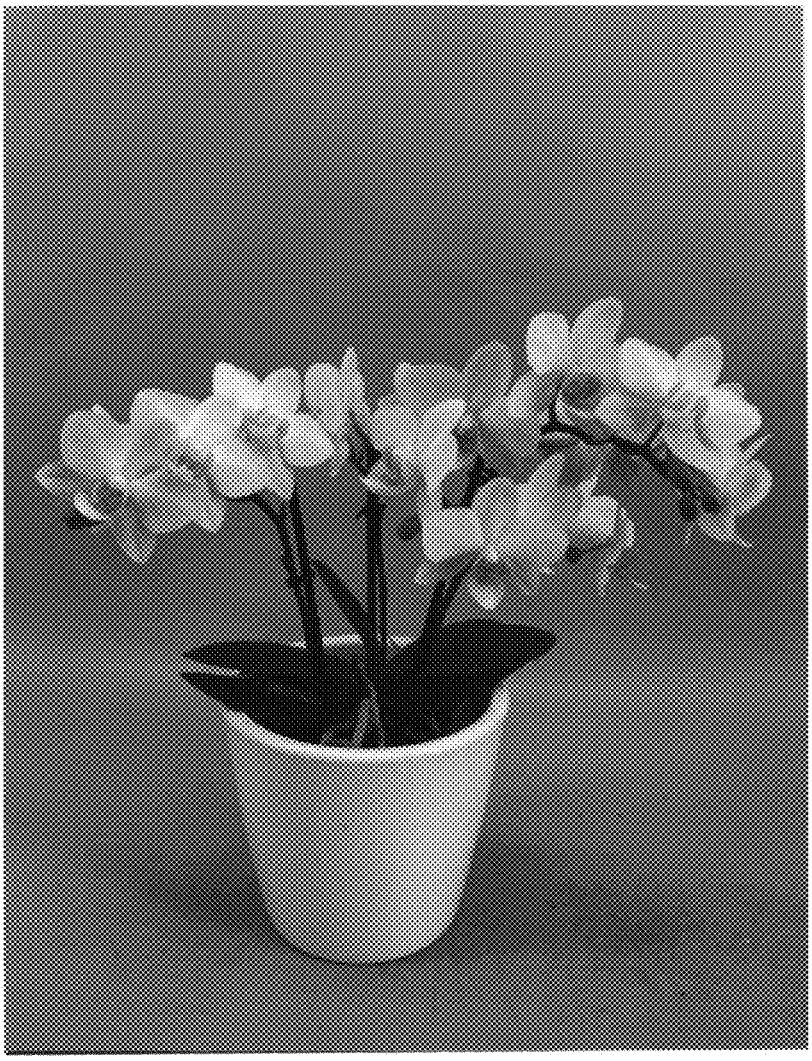
FIG. 1 shows the overall plant habit, including blooms, buds, and foliage of 'PHALOHCAE'.
Figure 2:
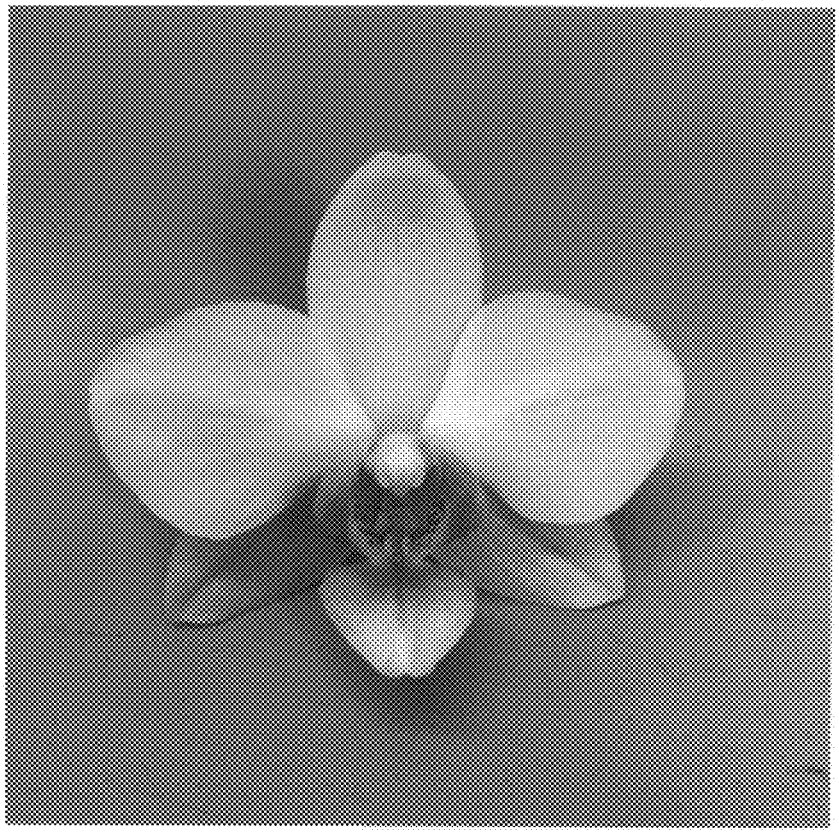
FIG. 2 shows a close-up of a flower of 'PHALOHCAE'.
Figure 3:
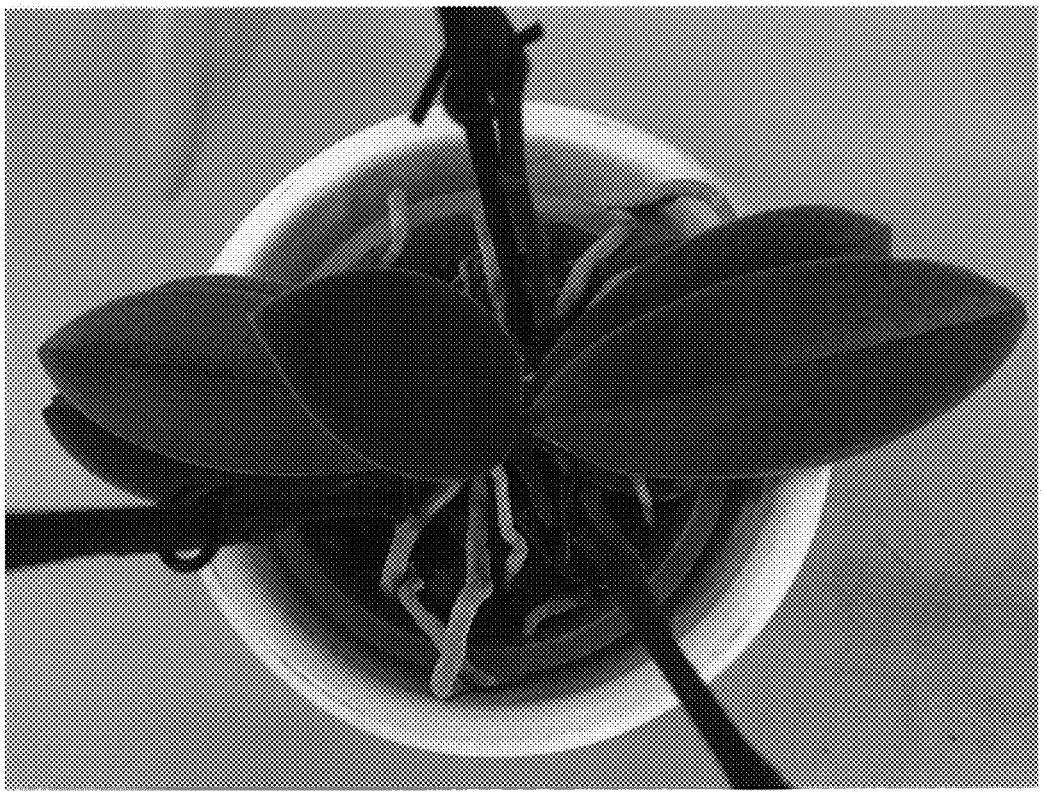
FIG. 3 shows an overhead view of the leaves of 'PHALOHCAE'.

The following detailed description sets forth the distinctive characteristics of 'PHALOHCAE'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in December 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALOHCAE'.

Parentage:

*Female parent*.—*Phalaenopsis* cultivar '21864-012' (unpatented).

*Male parent*.—*Phalaenopsis* cultivar '32980-05' (unpatented).

Propagation:

*Type*.—Meristem tissue culture.

Roots:

*Root description*.—Greyed-green (something between RHS 190B and 190C) colored roots with branching lateral roots having yellow-green (something in between RHS N144B and N144C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height (from soil level to top of inflorescence)*.—Approximately 20.0 cm to 25.0 cm.

*Width (measured from leaf tips)*.—About 21.0 cm to 23.0 cm. Plant is short and compact and grows as a single plant, but may develop one or two extra shoots.

*Vigor*.—Strong.

Leaves:

*Mature leaves*.—Quantity per plant: 9 to 11 leaves are produced before flowering. Length (fully expanded): 9.0 cm to 11.0 cm. Width: 3.5 cm to 4.5 cm. Position of broadest part of the leaf: At the middle. Shape: Narrow oblong. Base shape: Moderately to slightly elongated. Apex: Obtuse slightly asymmetric. Leaf blade angle with the petiole (measured from the horizontal position): Between 10 degrees and 20 degrees. Leaf margin: Entire. Color: Upper surface: RHS 147A. Lower surface: RHS 147B. Texture (both upper and lower surfaces): Smooth. Thickness: 1.8 mm to 2.1 mm. Variegation: Absent. Venation: Pattern: Parallel. Color of the midvein: Upper surface: RHS 147A. Lower surface: RHS 146A.

Peduncle:

*Quantity per plant*.—2 to 3.

*Number of flowers per peduncle*.—10 to 15.

*Length*.—20.0 cm to 25.0 cm.

*Diameter*.—3.0 mm to 4.0 mm.

*Strength*.—Strong.

*Aspect*.—Upright to slightly pendent.

*Texture*.—Smooth.

*Color*.—Green (something in between RHS 147A and 147B).

*Internode length*.—1.5 cm to 2.5 cm.

Inflorescence description:

*Appearance*.—Upright to slightly pendent, raceme and panicle inflorescence with bilaterally symmetrical flowers that open in succession beginning with the lowermost flower.

*Number of inflorescences*.—2 to 3.

*Inflorescence size*.—Height (from base to tip).—100.0 mm to 150.0 mm.

*Flowering time*.—First flowers can be expected 10 to 11 months after planting in a 12-cm pot.

*Flower*.—Height: 47.0 mm to 52.0 mm. Diameter: 55.0 mm to 60.0 mm. Depth of lip: About 16.0 mm to 18.0 mm.

*Flower longevity*.—On the plant: 15 to 17 weeks.

*Flower shape*.—Flat.

*Fragrance*.—Absent.

*Flower bud*.—Average size: Medium. Length: 18.0 mm to 20.0 mm. Width: 14.0 mm to 16.0 mm. Shape: Egg shaped. Color: Yellow-green (RHS N144C).

*Petals*.—Arrangement: Open. Shape: Semi-circular. Apex: Rounded asymmetric. Margin: Entire. Length (from base to tip): 26.0 mm to 28.0 mm. Width: 23.0 mm to 25.0 mm. Position of the broadest part of the petal: At the base. Color (when fully opened): Upper surface: Basic color: Yellow-green (RHS 154B). Over color: Absent. Lower surface: Basic color: Yellow-green (RHS 154B). Over color: Absent. Number of spots and stripes on the petals (upper surface): None. Color of spots and stripes on the petals (upper surface): Not applicable. Density of netting of the petals (upper surface): None. Color of the netting (upper surface): None.

*Dorsal sepal*.—Shape: Elliptic. Apex: Emarginated symmetric. Margin: Entire. Length (from base to tip): 28.0 mm to 30.0 mm. Width: 16.0 mm to 18.0 mm. Position of the broadest part of the dorsal sepal: At the middle. Color (when fully opened): Upper surface: Basic color: Yellow-green (RHS 154B). Over color: Light yellow-green (RHS 145C) at the middle from the base. Lower surface: Basic color: Yellow-green (RHS 154B). Over color: Yellowish-green (something in between RHS N144A and N144B). Number of spots and stripes on the dorsal sepals (upper surface): None. Color of spots and stripes on the dorsal sepals (upper surface): Not applicable. Density of netting of the dorsal sepals (upper surface): None. Color of the netting (upper surface): None.

*Lateral sepals*.—Shape: Ovate. Apex: Obtuse asymmetric. Margin: Entire. Length (from base to tip): 28.0 mm to 30.0 mm. Width: 17.0 mm to 19.0 mm.

Position of the broadest part of the lateral sepal: Toward the base. Color (when fully opened): Upper surface: Basic color: Yellow-green (RHS 154A). Over color: Diluting very small dots at the base (RHS 177C). Lower surface: Basic color: Yellow-green (RHS 154A). Over color: Yellowish-green (RHS N144A). Number of spots, dots, and stripes on the lateral sepals (upper surface): Few very small dots at the base. Color of spots, dots, and stripes on the lateral sepals (upper surface): RHS 177C. Density of netting of the lateral sepals (upper surface): None. Color of the netting (upper surface): None.

*Labellum* (*lip*).—Whiskers: Present, but very short. Length of whiskers: 1.0 mm to 2.0 mm. Color of whiskers: Light greenish-yellow (RHS 6B). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Slightly undulated. Length: 14.0 mm to 16.0 mm. Width: 8.0 mm to 10.0 mm. Color: Upper surface: Greenish-yellow (RHS 6C) at the base; striped (RHS 59A); yellow margin (RHS 9A) on one side; reddish-pink (something in between RHS 182B and 182C) and touch of white (RHS NN155C) toward the tip. Lower surface: Light greenish-yellow (RHS 4C) at the base; yellow margin (RHS 9B) and pink (RHS 182C) toward the tip. Number of spots and stripes on the lateral lobe: Medium stripes. Color of spots and stripes on the lateral lobe: RHS 59A. Density of netting of the lateral lobe: None. Color of the netting: None.

*Apical lobe*.—Shape: Ovate. Margin: Entire. Length: 16.0 mm to 18.0 mm. Width: 14.0 mm to 16.0 mm. Color: Upper surface: Red margin (RHS 176A) at the base; greenish-yellow (something in between RHS 6A and 151B); shaded (something in between RHS 176B and 176C) and dark purplish-pink (RHS 186C) toward whiskers. Lower surface: Red margin (RHS 176A) at the base; greenish-yellow wings (RHS 151B); light yellow-green (RHS 155B) at the middle toward whiskers. Number of spots and stripes on the apical lobe: None. Color of spots and stripes on the apical lobe: None. Density of netting of the apical lobe: None. Color of the netting: None. Bump and ridge: Present (medium).

*Callus*.—Average size: Very small to small. Height: 3.0 mm to 4 0 mm. Length: 2.0 mm to 3.0 mm. Width: 3.0 mm to 4.0 mm. Color: Orange-yellow tips (RHS 17A); light greenish-yellow (RHS 8B) on sides; dotted (RHS 175A).

Reproductive organs:

*Column*.—Length: 8.0 mm to 10.0 mm. Diameter: 3.8 mm to 4.3 mm. Color: White (RHS NN155B).

*Pollinia*.—Quantity: 2. Diameter: 0.7 mm to 0.9 mm. Color: Yellow-orange (RHS 23A).

*Ovary*.—Length: 8.0 mm to 10.0 mm. Diameter: 1.5 mm to 1.7 mm.

*Pedicel*.—Length: 28.0 mm to 30.0 mm. Diameter: 1.8 mm to 2.1 mm. Texture: Smooth. Color: Touch of green (RHS 147A) at the base; yellow-green (RHS 144B) and lighter yellow-green (RHS 144C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALOHCAE' differs from the female parent plant '21864-012' (unpatented) in that 'PHALOHCAE' has weakly spatulate lateral lobes, ovate apical lobes, and very short whiskers, whereas '21864-012' has oblong lateral lobes, narrowly rhombic apical lobes, and no whiskers.

'PHALOHCAE' differs from the male parent plant '32980-05' (unpatented) in that 'PHALOHCAE' has weakly spatulate lateral lobes and flowers with a main color of yellow-green, whereas '32980-05' has spatulate lateral lobes and flowers with a main color of white.

'PHALOHCAE' is most similar to the commercial *Phalaenopsis* plants named 'PHALFOMZYN' (U.S. Plant Pat. No. 31,947) and 'PHALGALYI' (U.S. Plant Pat. No. 31,051). 'PHALOHCAE' differs from the commercial variety 'PHALFOMZYN' in that 'PHALOHCAE' has light greenish-yellow whiskers, white columns, and emarginated dorsal sepal apexes, whereas 'PHALFOMZYN' has white whiskers, columns that are very light purple at the base and white toward the tip, and obtuse dorsal sepal apexes.

'PHALOHCAE' differs from the commercial variety 'PHALGALYI' in that 'PHALOHCAE' has emarginated dorsal sepal apexes, whereas 'PHALGALYI' has rounded dorsal sepal apexes with the tip slightly folded toward the back. Additionally, 'PHALOHCAE' has narrower leaves than 'PHALGALYI'.

I claim:

1. A new and distinct variety of *Phalaenopsis* plant named 'PHALOHCAE', substantially as described and illustrated herein.

* * * * *